United States Patent [19]

Stansfeld

[11] 4,007,627
[45] Feb. 15, 1977

[54] DENSITY TRANSDUCERS

[75] Inventor: James Woolryche Stansfeld, Beech, near Alton, England

[73] Assignee: The Solartron Electronic Group Limited, Hampshire, England

[22] Filed: Sept. 18, 1975

[21] Appl. No.: 614,574

[30] Foreign Application Priority Data

Sept. 21, 1974 United Kingdom ............ 41208/74

[52] U.S. Cl. ............................................. 73/32 A
[51] Int. Cl.² ........................................ G01N 9/00
[58] Field of Search .................................. 73/32 A

[56] References Cited

UNITED STATES PATENTS

| 3,218,851 | 11/1965 | Sipin | 73/32 A X |
| 3,444,723 | 5/1969 | Wakefield | 73/32 A |
| 3,618,360 | 11/1971 | Curtis | 73/32 A |

Primary Examiner—James J. Gill
Attorney, Agent, or Firm—William R. Sherman; Kevin McMahon

[57] ABSTRACT

A density transducer employs a hollow cylinder capable of vibrating in the circumferential (or hoop) mode as the density sensing element, the cylinder being open at both ends and arranged so that the fluid whose density is to be transduced can come into contact with only the internal surface of the cylinder. The opposite ends of the cylinder are each secured to a respective clamping ring, which establishes a node at its respective end of the cylinder. The clamping rings each have a piston face which faces axially away from the cylinder and is acted on by the pressure of the fluid, thereby applying a compressive axial force to the cylinder which tends to reduce the effect of variations in the pressure of the fluid on the frequency of the vibration.

11 Claims, 6 Drawing Figures

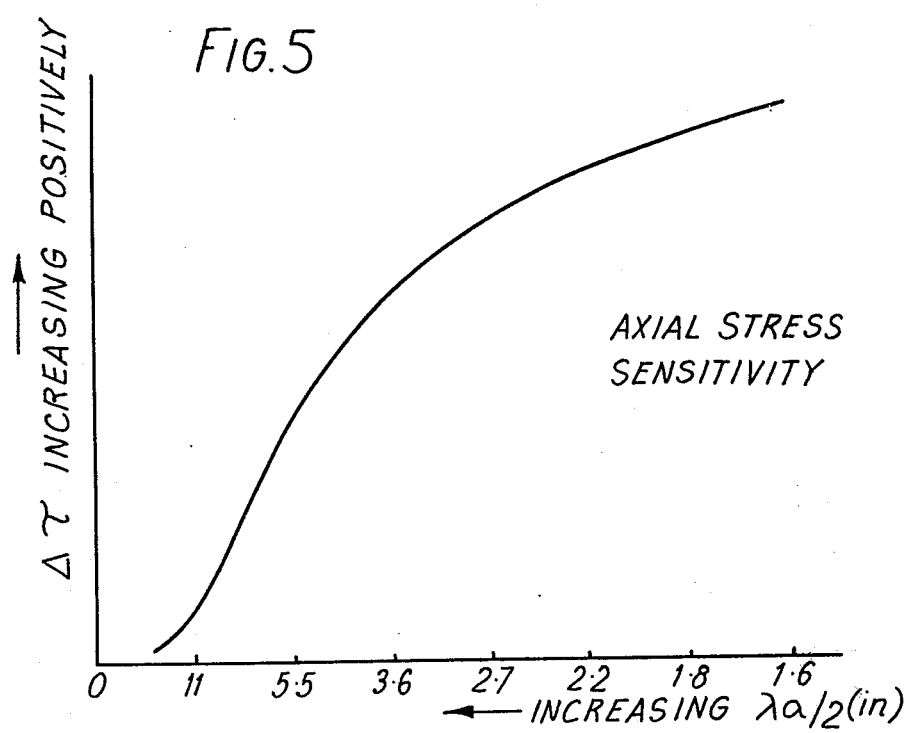
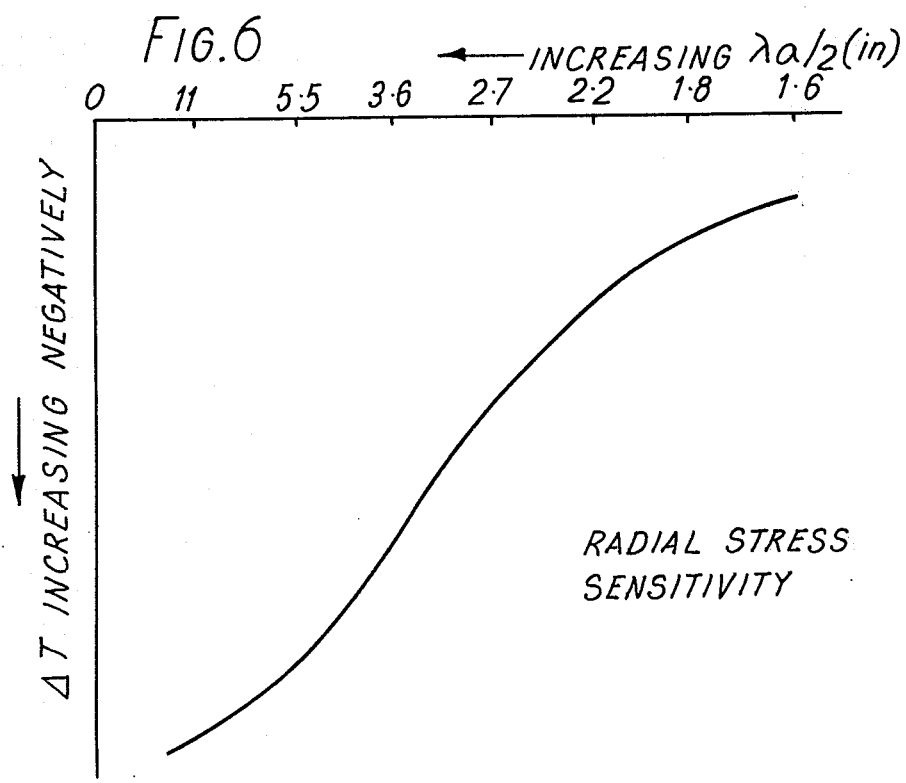

DENSITY TRANSDUCERS

This invention relates to apparatus for measuring the density of fluids.

It is known that the frequency of the resonant circumferential or "hoop mode" vibrations when a hollow cylinder or tube of resilient material is resonated vary with the density of the fluid which is in contact with the wall of the vibrating cylinder. And density transducers are known which exploit this phenomenon, the resonant frequency of the cylinder in the presence of the fluid being used as a measure of the density of the fluid.

If the cylinder wall is subjected to stress due to the pressure of the fluid, acting radially on the wall, the resonant frequency will change; this change in frequency will be interpreted as a change in density thereby causing an error in the density measurement. In order to attempt to reduce this unwanted change of frequency with pressure, or "pressure coefficient," density meters of this type have been arranged so that the fluid whose density is to be measured comes into contact with both the inner and the outer wall of the cylinder, so that there is no differential pressure exerted across the cylinder wall, and hence no radial stress due to pressure. However this solution leads to a density meter whose accuracy and operation can be degraded by deposition on both sides, particularly the outer side of the cylinder of suspended particles carried by dirty fluids, in particular dirty liquids. Also, in some configurations such a density meter can be sensitive to changes in viscosity of the fluid being measured, the magnitude of the sensitivity to viscosity being dependent upon the total surface area of the cylinder in contact with the fluid.

It is an object of the present invention to provide a density meter using a hollow cylinder as the density measuring element, in which the pressure coefficient is significantly reduced and which has an acceptable viscosity coefficient.

According to one aspect of the present invention, therefore, there is provided a density transducer for producing an output signal representative of the density of a fluid, comprising a hollow circumferentially vibratable cylinder arranged so that the fluid can come into contact with only one of its internal and external surfaces, means for exciting and maintaining circumferential resonant vibration of the cylinder and for producing an output signal representative of the frequency of said vibration, and means responsive to the pressure of the fluid to apply a compressive axial force dependent upon said pressure to the cylinder, whereby to reduce the effect of variations of the pressure of the fluid on the frequency of said vibration.

According to another aspect of the present invention, there is provided a density meter using a hollow cylinder as the density measuring element, in which the fluid can come into contact with only the inner surface of the cylinder wall, and in which the pressure of the fluid is arranged to apply a compressive axial force to the cylinder, thereby reducing the pressure coefficient of the density meter.

According to yet another aspect of the invention, a transducer for measuring the density of a fluid comprises:

a hollow right circular cylinder, open at both ends so as to permit the fluid whose density is to be measured to enter and leave the cylinder and come into contact with the inner wall thereof, this cylinder being made of or carrying a ferromagnetic material and being capable of being set and maintained in circumferential resonant vibration;

a pair of relatively massive clamping rings secured one to each end respectively of the cylinder so as to hold the cylinder firmly and establish a node at each end;

means including the clamping rings for preventing the fluid from coming into contact with the outer wall of the cylinder; and a magnetic drive assembly comprising at least one drive coil and at least one pick-up coil disposed outside the cylinder (but near enought to interact with the ferromagnetic material constituting or carried by its wall), said pick-up coil being connected to the drive coil, the arrangement being such as to maintain the cylinder in its natural (resonant) circumferential vibration in a predetermined mode, whereby the frequency of vibration is a measure of the density of the fluid inside the cylinder;

said clamping rings being mounted in a housing, at least one of them by means of a flexible connection which permits that ring to exert an axial force on the cylinder;

the or each flexibly mounted clamping ring having a piston face facing axially outward of the cylinder and arranged to be acted on by the pressure of the fluid whereby the ring transmits the resulting axially compressive force to the cylinder; and the piston face and the cylinder being dimensioned such that the axially compressive force so transmitted to the cylinder tends to compensate for (unwanted) variation in the frequency of vibration due to the effect of the fluid pressure on the inner wall of the cylinder.

The invention will be further described by way of example with reference to the accompanying drawings in which:

FIG. 5 is a graph showing the axial load sensitivity of a vibrating cylinder such as illustrated in FIGS. 1-4, as a function of the length of the cylinder, and FIG. 6 is a graph showing the pressure sensitivity of such a cylinder, also as a function of its axial length.

Figure 1:
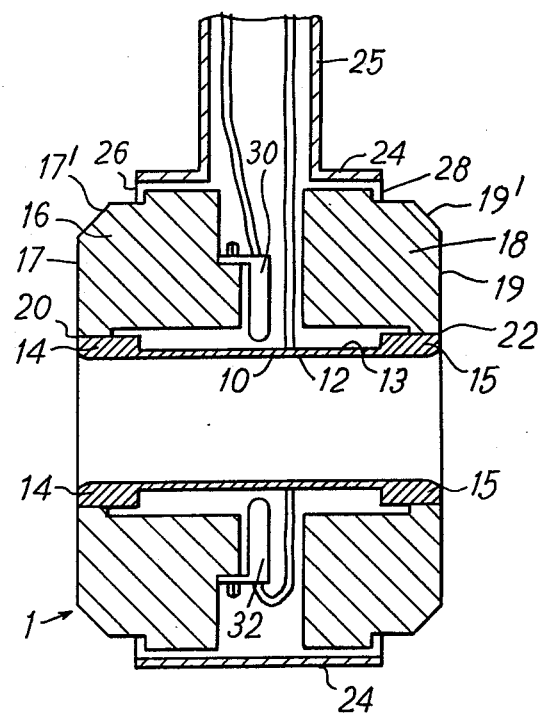
FIG. 1 is an axial section of one embodiment of a density transducer in accordance with the invention, arranged for insertion in the fluid whose density is to be measured.

The density transducer shown in FIG. 1 is intended for insertion in the fluid (liquid, in particular) whose density is to be measured and comprises a hollow right circular cylinder 10 open at both ends so as to permit the fluid to enter and leave the cylinder and to come into contact with the inner wall 12 thereof. The cylinder 10 is capable of being set and maintained in resonant circumferential vibration (described in detail with reference to FIGS. 3 and 4), the frequency of which is used as the measure of the density of the fluid. The cylinder 10 is formed with integral external flanges 14, 15 at its ends, and may conveniently be formed by grinding down the outer surface of a piece of tube stock between the flanges 14 and 15. The cylinder is advantageously made of a ferromagnetic metal so as to be able to interact directly with a magnetic drive assembly (to be described later on), and preferably the material constituting the cylinder has a low coefficient of thermal expansion, for thermal stress in the cylinder degrades the measurement. An appropriate material is Ni-Span C, which satisfies both these criteria.

A pair of relatively massive clamping rings 16 and 18 are electron beam welded at 20 and 22 to the external flanges 14 and 15 respectively near their outer ends. The clamping rings 16 and 18 thereby hold the cylinder 10 firmly and establish a node at each end of this cylinder.

The clamping rings 16 and 18 are mounted in a generally cylindrical body 24 by means of flexible ligaments 26 and 28 respectively. These flexible ligaments each comprise a piece of sheet metal of annular shape, the inner edges of the annular ligaments being welded to peripheral surfaces of the clamping rings and the outer edges being welded to the body 24. The sheet metal ligaments 26 and 28 are relatively flexible in the axial direction of the cylinder 10 and therefore permit the clamping rings 16 and 18 to apply an axial force on the cylinder 10. However the ligaments 26 and 28 are of sufficient size in the radial dimension to be relatively stiff in this direction so as to substantially prevent the clamping rings 16 and 18 from moving radially inside the body 24. The body 24 is provided with a hollow shaft or handle 25 by which the transducer can be held during immersion in the fluid to be measured.

The clamping rings 16 and 18, which are welded in a fluid-tight manner to the outer ends of the cylinder 10, together with the flexible ligaments 26 and 28 and the body 24, prevent the fluid from coming into contact with the outer wall 13 of the cylinder 10. The transducer thus operates with the fluid to be measured in contact with the inner cylinder wall 12 but not in contact with the outer cylinder wall 13. Any difference between the pressure of the fluid inside the cylinder and the pressure prevailing outside the cylinder (this latter pressure may for example be atmospheric pressure), will generate a pressure differential across the cylinder wall which puts the cylinder wall under radial stress and tends to make the frequency of vibration vary as a function of pressure — in addition to the desired variation in frequency as a function of density. The means for minimizing this pressure coefficient are described later on.

Figure 4:
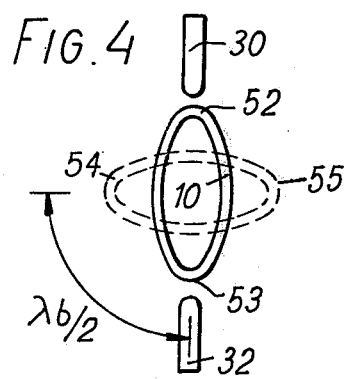
FIG. 4 is a cross-section along the line IV—IV of FIG. 3, showing against these two extreme positions of the circumferential vibration.

The cylinder 10 is maintained in resonant circumferential vibration in a predetermined mode by means of a magnetic drive assembly comprising a drive coil 30 and a pickup coil 32. These coils 30 and 32 are mounted on one of the clamping rings 16, in the space between that clamping ring and the other clamping ring 18. The coils are disposed with their axes on a common diametral line of the cylinder 10, half way between the ends of the cylinder and at positions on the circumference of the cylinder which correspond to natural antinodes as shown in FIG. 4 (these preferential positions for the antinodes occur because the cylinder is never perfectly symetrical rotationally about its axis). As the coils are mounted outside the cylinder 10, they are protected from fluid whose density is to be measured and in addition they do not obstruct or impede the flow of fluid through the transducer; this latter point is more important in the flow-through arrangement of the embodiment of FIG. 2. The magnetic couplng between the coils themselves is very slight in the arrangement shown in the drawings, and this is advantageous.

The pick-up coil 30 is connected via leads 33 to the input of an amplifier 34 whose output is connected via leads 35 to the drive coil 32. The amplifier 34 is located remote from the rest of the transducer, and the leads 33 and 35 pass out through a hole in the body 24 and through the interior of the hollow shaft 25 fastened to the body 24 around this hole. Conveniently, the amplifier 34 can be housed in a box 36 mounted on the end of the shaft 25. The motion of the ferromagnetic cylinder 10 in the vicinity of the pick-up coil 30 (see FIGS. 3 and 4) generates a corresponding electrical signal in the pick-up coil. This signal is amplified in the amplifier 34 and the amplified signal is applied to the drive coil 32 which drives the cylinder wall adjacent thereto, thereby maintaining the vibration. The amplifier 34 is designed to introduce the appropriate phase shift between the pick-up signal and the drive signal in order to sustain the vibration. The design of such an amplifier is well known in this art. The amplifier 34 is provided with a signal output terminal 37 which can be connected to a frequency meter (not shown). The frequency of the output signal appearing at 37 is the same as the frequency of vibration of the cylinder 10, so that the frequency reading given by the meter is representative of the density of the fluid in contact with the cylinder.

As mentioned above, any pressure in the fluid will be exerted on the inner wall 12 of the cylinder 10 (but not on the outer wall 13 of this cylinder since the fluid is prevented from coming in contact with this outer wall), and this pressure sets up a radial stress in the cylinder which tends to make the resonant frequency of vibration change, which would be interpreted as a change in the density of the fluid. In order to compensate for this unwanted pressure coefficient, i.e., frequency change as a function of pressure, the clamping rings 16 and 18 are each provided with a face 17 and 19 respectively directed axially outward of the cylinder 10. These faces 17 and 19 are subjected to the same fluid pressure as the inner wall 12 of the cylinder, and they act as piston faces converting that pressure into an axial compressive force which is transmitted by the clamping rings 16 and 18 to the cylinder 10 to which these rings are secured. The piston faces 17 and 19 have chamferred outer edge portions 17' and 19' which also contribute to the generation of the axial force, although their contribution is reduced by a factor involving the cosine of the angle the chamfer makes with the main portion of the piston face 17 or 19. The effect of this axial compressive force on the cylinder 10 is to tend to make the resonant frequency of vibration change, but in the opposite sense to the change caused by the pressure acting radially on the inner cylinder wall 12. The magnitude of the axial force applied to the cylinder is of course directly proportional to the effective area of the piston faces 17 and 19 (including the contribution of the chamferred portions 17' and 19'). The effects of the radial and axial stresses on the resonant frequency of the cylinder will be described in more detail later on with reference to FIGS. 5 and 6.

Figure 2:
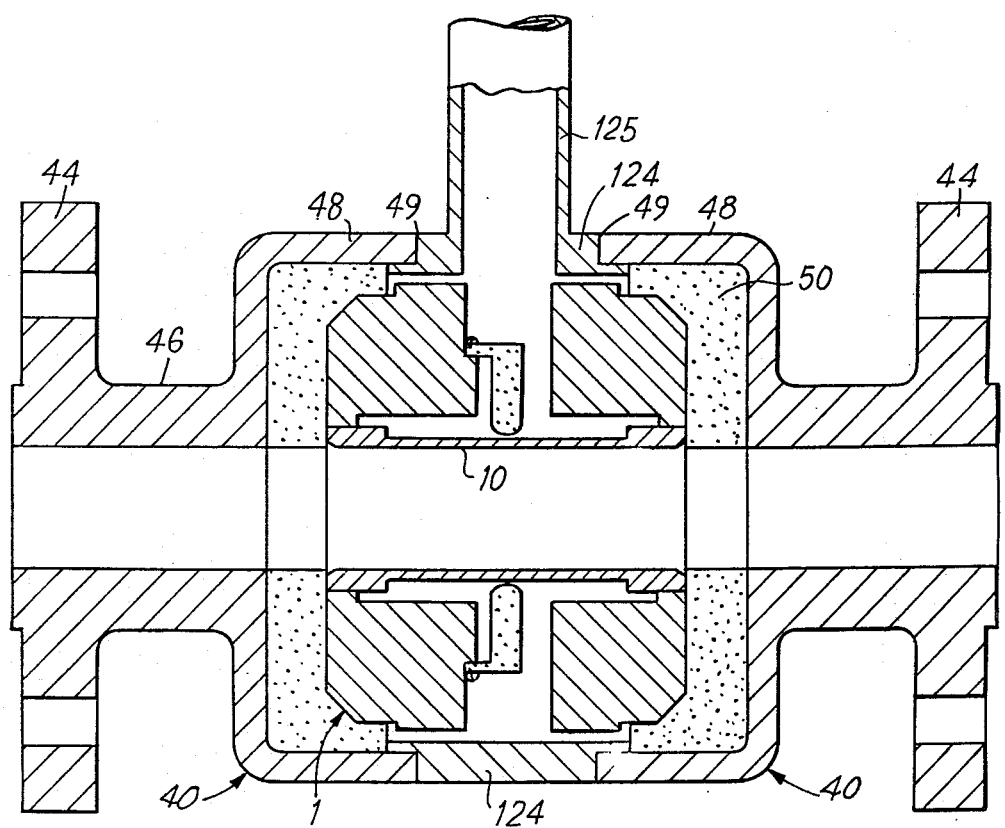
FIG. 2 is an axial section of another embodiment of a density transducer in accordance with this invention, arranged to have the fluid flow continuously therethrough.

Turning now to FIG. 2, this figure shows another arrangement of a density transducer in accordance with this invention. In this arrangement the transducer is mounted "on line" in a pipe (not shown) carrying the fluid whose density is to be measured, and the fluid flows continuously through the transducer. The transducer of FIG. 2 — generally designated by the reference numeral 1 — is very similar to the transducer shown in FIG. 1, and the same reference numerals have been used to designate the identical elements. The only difference is in the body and the shaft, and these have been designated 124 and 125 respectively in the transducer of FIG. 2. The shaft 125, which in this embodiment does not have to serve as a handle since the transducer is not intended for insertion in the fluid, can be significantly shorter than in the embodiment of FIG. 1. And the body 124 is adapted to fit into and mate with a coupling — generally designated 40 — by which the transducer is mounted in the aforementioned pipe. The coupling 40 has a pair of end flanges 44 which are fastened to corresponding end flanges 42 welded on the adjacent ends of the pipe 41. The coupling 40 also comprises short tubular portions 46 extending axially inward from the end flanges 44 respectively and leading to a central housing portion 48 which mates with and is welded to the body 124 at 49. The housing 48 generally surrounds the transducer 1, but a space is provided between the housing and the clamping rings 16 and 18, so as to allow the fluid whose density is to be measured to act on the piston faces 17, 17' and 19, 19'.

If desired, as shown in FIG. 2, this space between the housing 48 and the clamping rings 16 and 18, their corresponding flexible ligaments 26 and 28 and the end surfaces of the cylinder 10 can be filled with a resilient substance such as silicon rubber, shown at 50. This does not affect the axial load applied to the cylinder 10 to compensate for the radial pressure effects on the cylinder, for the resilient substance acts as an extension of the fluid and applies the same pressure to the piston faces 17, 17' and 19, 19' of the clamping rings as the fluid would do in the absence of this substance. The resilient silicon rubber substance 50 prevents solid matter in the fluid from depositing and getting clogged in the space occupied by this rubber. Furthermore, in the arrangement shown in FIG. 2 in which the cylinder 10 and the coupling tubular portions 46 (as well as the pipeline 41) have the same internal diameter, the rubber 50 provides a smooth, continuous bore, which facilitates the through flow of the fluid.

The transducers shown in FIGS. 1 and 2 are intended for measuring the density of liquids, although there is no reason why the present invention could not be used for a gas density transducer as well. The principal difference is that in a gas density transducer, the wall of the cylinder 10 would be considerably thinner.

Figure 3:
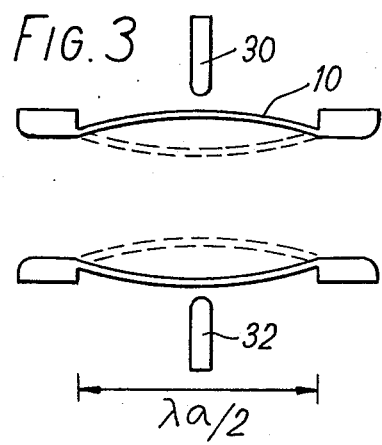
FIG. 3 is an axial section of the vibrating cylinder of the transducers of FIGS. 1 and 2, showing the position of the cylinder wall at a vibration "peak" and also at a vibration "trough" (the amplitude of the vibration being greatly exaggerated for clarity), illustrating the circumferential or "hoop mode" vibration of this cylinder.

The circumferential vibration of the cylinder will now be described with reference to FIGS. 3 and 4, in which the amplitude of the vibration is greatly exagerated for the sake of clarity. In these figures, the cylinder 10 is shown in solid lines in one extreme position of the vibration corresponding to a "peak" in the wave form, and the cylinder is shown in broken lines in the other extreme position of the vibration, corresponding to a "trough" in the wave form. The preferred mode of this circumferential vibration is the simplest mode, and this is what is illustrated in FIGS. 3 and 4. As seen in FIG. 3, the axial half wave length $\lambda a/2$ is equal to the length of the cylinder 10 contained between the flanges 14, 15, which by reason of their increased thickness and above all because they are clamped to the relatively massive rings 16 and 18 form nodes. Thus the axial component of the vibration is vibrating in which can be thought of as the fundamental mode.

FIG. 4 shows the cylinder 10 in cross section, and it can be seen that at a vibration peak (solid lines), there are two lobes 52 and 53 diametrically opposite each other, and in the trough position (dotted lines) there are also two diametrically opposed lobes 54 and 55 offset from the lobes 52 and 53 by 90°. The half wave length $\lambda b/2$ of the circumferential component of the vibration is equal to one quarter of the distance around the circumference of the cylinder.

The drive and pick-up coils 30 and 32 are positioned half-way between the ends of the cylinder at points adjacent to the lobes 52 and 53. Although two coils are sufficient to maintain the circumferential vibration in this preferred and simplest mode, they cannot prevent the vibration from jumping into a higher mode at twice the frequency, for in that higher mode, the points 52 and 53 are still in phase. However this frequency doubling can be eliminated by filtering at the amplifier 34 in a manner known per se. Alternatively, frequency doubling can be avoided by using three coils, either two pick-up coils and one drive coil or two drive coils and one pick-up coil, these three coils being positioned at three of the four points 52–55 of maximum movement. This ensures that the drive and pick-up coils are 90° out of phase so that the phase shift introduced by the amplifier is sufficient to maintain the correct mode of vibration. If the frequency were to double, these coils would have to be in phase and this is prevented by the amplifier.

Although the simplest mode of vibration is preferred, it is possible to operate at a higher mode, particularly in the circumferential component. Instead of just two lobes at each peak and trough position, there could be three or four lobes for example, the drive and pick-up coils being positioned at some or all of these lobes. Similarly, it is theoretically possible to operate at a higher mode in the axial component of vibration.

The density sensitive element 10 shown in FIGS. 1 to 4 is a hollow cylinder having a uniform wall thickness between the end flanges 14 and 15. As a variant, the longitudinal nodal lines (nodal with respect to the circumferential component of vibration) could be left thicker than the anti-nodal portions (52 to 55 in FIG. 4). This has the effect of strengthening the cylinder which, it will be recalled, is going to be subjected to an axial load in use. It also has the effect of tending to stabilize the mode of vibration by helping to define the positions of the longitudinal nodes of the anti-nodes.

The effects of radial pressure stress on the inner wall of the cylinder 10 and the effects of axial stress on the cylinder will now be described with reference to FIGS. 6 and 5 respectively. FIG. 6 is a graph of $\Delta T$ the percent change in the period of the resonant vibrations of the cylinder (the reciprocal of the frequency) per unit pressure change versus $\lambda a/2$ the axial half wavelength of resonance of the cylinder. FIG. 5 is a graph of $\Delta \tau$ the percent change in the period of the resonant vibrations of the cylinder per unit axial compressive load versus $\lambda a/2$ the axial half wavelength of resonance. In both cases the cylinder was vibrated in its simplest mode of circumferential vibration as shown in FIGS. 3 and 4. Thus the axial half wave length $\lambda a/2$ is equal to the active length of the vibrating cylinder between its end flanges, and the circumferential half wave length $\lambda b/2$ is constant. All the other parameters of the cylinder were also held constant. The cylinder used in preparing the graphs of FIGS. 5 and 6 had an inside diameter of 0.875 inches, a wall thickness of 0.037 inches and was made of Ni-span C 902 (Trade Mark). It should be noted in both graphs that $\lambda a/2$ increases from right to left from about 1.6 inches at the right hand end to about 11 inches at the left hand end.

It can be seen from FIG. 6 that the effect of radial stress on the cylinder due to the fluid pressure on the inner wall of this cylinder is to make the period of the resonant vibration decrease (i.e., to make the frequency increase). The percent change (decrease) in the period increases as $\lambda a/2$ increases. That is, the longer the cylinder, the greater its sensitivity to radial pressure stress.

In FIG. 5 it can be seen that the effect of an axial compressive stress on the cylinder due to the action of the piston faces 17 and 19 (FIGS. 1 and 2) when the fluid pressure is exerted on these faces, is to make the period of resonant vibration increase (i.e., to make the resonant frequency decrease). It will be noted that this change (increase) in period is in the positive direction, whereas the change (decrease) in period due to radial stress (FIG. 6) is in the negative direction. It is this fact that allows the axial compression of the cylinder to compensate for the fluid pressure effect on the inner wall of the cylinder. FIG. 5 also shows that the sensitivity of the cylinder to axial load decreases as $\lambda a/2$ increases. This is opposite to the radial stress sensitivity shown in FIG. 6, which, as seen above, increases with increasing $\lambda a/2$. This enables the compensation due to the axial load to be optimised by choosing the appropriate length $\lambda a/2$ for the cylinder, having regard to the other dimensions of the transducer.

The above explanation given with reference to FIGS. 5 and 6 of the effects of compressive axial load and outwardly-directed radial pressure stress on the vibrating density sensitive cylinder, and in particular of how the axial compressive load is used in accordance with the present invention to compensate for the unwanted effects of the fluid pressure on the inner wall of the cylinder, is only valid for circumferential vibration of the cylinder, although this circumferential vibration does not necessarily have to be in the simplest mode shown in FIGS. 3 and 4.

As a practical matter in designing a density transducer in accordance with this invention, one can start by defining the overall size of the transducer; generally it is desired to have the transducer as small as practicable, as a matter of convenience, and the maximum dimension may be set at, say, 6 inches for example.

Turning next to the cylinder, it is generally convenient to work with a cylinder that is not too small, and a cylinder of the order of 1 inch in diameter is generally convenient. The wall thickness of the active, vibrating portion of the cylinder is then determined so as to give the transducer the desired sensitivity to density changes. For example, it is convenient to arrange for the frequency to change by about 25 per cent, say, from zero to full scale of the density range being measured, and it is the wall thickness that determines how great this change will be. Of course the mechanical strength of the cylinder must also be borne in mind since the cylinder is going to be subjected to an axial load. The area of the piston faces 17 and 19 (FIGS. 1 and 2) is then set as large as possible consistent with the maximum overall size already defined for the transducer. Finally, the length of the cylinder is determined so as to optimize the compensation for the pressure effects by means of the axially applied compressive force exerted on the cylinder by the piston faces.

In another embodiment of this invention, instead of optimising the compensation so as to minimise the pressure effects, the length of the cylinder can be chosen so as to obtain a particular pressure coefficient to offset the compressibility factor of liquids and thereby achieve relative density measurements.

In the embodiments described above, the principle of the present invention that the frequency of the vibrating cylinder is sensitive to axial force has been applied to provide pressure compensation in a density transducer. This principle can also be exploited directly to make a pressure transducer or load cell in which the change in frequency is used as a measure of the pressure of load (force) acting axially on the cylinder to compress it. For this application it is simply necessary to extend the piston faces 17 and 19 of FIG. 1 across the ends of the cylinder, thereby sealing off the cylinder and preventing the pressure medium from coming into contact with the inner wall of the cylinder (it has already been excluded from the outer wall). The output frequency can then be calibrated directly in units of force or pressure (force divided by the area of the piston faces.

Several modifications can be made to the described embodiments of the invention. In particular, the transducer can be modified so that the fluid comes into contact with only the outer surface of the cylinder 10, for example by arranging the drive and pick-up coils inside the cylinder. In this case, some reduction of the sensitivity of the transducer to both deposits from, and the viscosity of, the fluid is still obtained, by virtue of the reduction of the area of the cylinder 10 in contact with the fluid.

What is claimed is:

1. A density transducer for producing an output signal representative of the density of a fluid, comprising a hollow circumferentially vibratable cylinder arranged so that the fluid can come into contact with only one of its internal and external surfaces, means for exciting and maintaining circumferential resonant vibration of the cylinder and for producing an output signal representative of the frequency of said vibration, and means responsive to the pressure of the fluid to apply a compressive axial force dependent upon said pressure to the cylinder, whereby to reduce the effect of variations of the pressure of the fluid on the frequency of said vibration.

2. A transducer as claimed in claim 1, wherein said one of the internal and external surfaces is the internal surface of the cylinder.

3. A transducer as claimed in claim 2, wherein the cylinder is open at both ends to permit the flow of fluid therethrough.

4. A transducer as claimed in claim 3, wherein the cylinder is disposed in a housing, and wherein the pressure responsive means comprises a pair of relatively massive clamping rings secured one to each end of the cylinder, thereby establishing a respective node at each end of the cylinder, and flexible mounting means for flexibly connecting at least one of the clamping rings to the housing, the or each flexibly mounted clamping ring having a piston face facing axially away from the cylinder and arranged to be acted on by the pressure of the fluid.

5. A transducer as claimed in claim 4, wherein the flexible mounting means comprises respective flexible mounting members for flexibly connecting each clamping ring to the housing.

6. A transducer as claimed in claim 5, wherein the housing is substantially cylindrical and coaxially surrounds the cylinder, and wherein each flexible mounting member comprises an annular member which extends radially across the annular space between the cylinder and the housing and which is sealingly connected to both the housing and its respective clamping ring, thereby preventing the fluid from coming into contact with the external surface of the cylinder.

7. A transducer as claimed in claim 4, wherein the housing includes at opposite ends thereof respective end portions each containing a bore which is coaxially aligned with, axially spaced from, and of substantially the same diameter as, the cylinder, whereby the fluid can enter the housing via one of the bores, flow through the cylinder and leave the housing via the other bore, and wherein the end portions are connected to the remainder of the housing via respective radially outwardly extending walls each axially spaced from a respective one of the clamping rings.

8. A transducer as claimed in claim 7, wherein the annular space between each wall and the piston face of the adjacent clamping ring is filled with a resilient fluid-pressure-transmitting solid material.

9. A transducer as claimed in claim 8, wherein said resilient fluid-pressure-transmitting solid material is a silicone rubber.

10. A transducer as claimed in claim 1, wherein the cylinder is made from a ferromagnetic material, and wherein the means for exciting and maintaining circumferential resonant vibration of the cylinder comprises at least one drive coil and at least one pick-up coil disposed adjacent the external surface of the cylinder, the pick-up coil being connected to the input of an amplifier which has an output connected to the drive coil so as to maintain said resonant circumferential vibration of the cylinder.

11. A density transducer comprising:
a hollow right circular cylinder, open at both ends so as to permit the fluid whose density is to be measured to enter and leave the cylinder and come into contact with the inner wall thereof, the cylinder being made of a ferromagnetic material and being capable of being set and maintained in circumferential resonant vibration;
a pair of relatively massive clamping rings secured one to each end respectively of the cylinder so as to hold the cylinder firmly and establish a node at each end;
means including the clamping rings for preventing the fluid from coming into contact with the outer wall of the cylinder; and
a magnetic drive assembly comprising at least one drive coil and at least one pick-up coil disposed outside the cylinder, but near enough to interact with the ferromagnetic material constituting or carried by its wall, said pick-up coil being connected to the input of a maintaining amplifier whose output is connected to the drive coil, the arrangement being such as to maintain the cylinder in resonant circumferential vibration in a predetermined mode, whereby the frequency of vibration is a measure of the density of the fluid inside the cylinder;
said clamping rings being mounted in a housing, at least one of them by means of a flexible connection which permits that ring to exert an axial force on the cylinder;
the or each flexibly mounted clamping ring having a piston face facing axially outward of the cylinder and arranged to be acted on by the pressure of the fluid whereby the ring transmits the resulting axially compressive force to the cylinder; and
the piston face and the cylinder being dimensioned such that the axially compressive force so transmitted to the cylinder tends to compensate for unwanted variation in the frequency of vibration due to the effect of the fluid pressure on the inner wall of the cylinder.

* * * * *

UNITED STATES PATENT OFFICE
CERTIFICATE OF CORRECTION

Patent No. 4,007,627                Dated  February 15, 1977

Inventor(s)  James Woolryche Stansfeld

It is certified that error appears in the above-identified patent and that said Letters Patent are hereby corrected as shown below:

IN THE SPECIFICATION:

Column 6, line 53 after "nodes" delete "of the" and substitute therefor -- and --.

Column 8, line 28, after "faces" insert --)--.

Signed and Sealed this

Eighteenth Day of April 1978

[SEAL]

Attest:

RUTH C. MASON
Attesting Officer

LUTRELLE F. PARKER
Acting Commissioner of Patents and Trademarks